(12) United States Patent
Fischvogt et al.

(10) Patent No.: US 12,310,648 B2
(45) Date of Patent: May 27, 2025

(54) ELECTROSURGICAL INSTRUMENTS INCLUDING A JAW ANGLE DETECTION SYSTEM

(71) Applicant: Covidien LP, Mansfield, MA (US)

(72) Inventors: Gregory W. Fischvogt, Reno, NV (US); Jenna Dancy, Longmont, CO (US); Hayden W. May, Westminster, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/595,655

(22) Filed: Mar. 5, 2024

(65) Prior Publication Data

US 2024/0197386 A1    Jun. 20, 2024

Related U.S. Application Data (62) Division of application No. 16/944,367, filed on Jul. 31, 2020, now Pat. No. 11,931,097.

(Continued)

(51) Int. Cl.
*A61B 17/00* (2006.01)
*A61B 18/14* (2006.01)
(Continued)

(52) U.S. Cl.
CPC .... *A61B 18/1445* (2013.01); *A61B 2017/00017* (2013.01); *A61B 2017/00734* (2013.01);
(Continued)

(58) Field of Classification Search
CPC ............................ A61B 18/1445; A61B 34/25
See application file for complete search history.

(56) References Cited

U.S. PATENT DOCUMENTS 7,156,846 B2   1/2007   Dycus et al.
8,034,049 B2  10/2011   Odom et al.
(Continued)

FOREIGN PATENT DOCUMENTS

CN   107847264 A   3/2018
JP   S57139613 A   8/1982
(Continued)

OTHER PUBLICATIONS

European Search Report dated Jan. 19, 2021, issued in corresponding European Appl. No. 20191181, 10 pages.
(Continued)

*Primary Examiner* — Mallika D Fairchild
*Assistant Examiner* — Thien Jason Tran (57) ABSTRACT

An electrosurgical instrument includes an elongated shaft, an end effector, a drive shaft, and a switch assembly. The end effector is coupled to a distal end portion of the elongated shaft and includes opposing first and second jaw members. The end effector is configured to move between an open configuration and a closed configuration. The drive shaft is operably coupled to the end effector to move the end effector between the open and closed configurations. The switch assembly includes a first electrical contact and a second electrical contact. The first electrical contact is coupled to the drive shaft and configured to move with the drive shaft. The first electrical contact is configured to engage the second electrical contact in response to a movement of the drive shaft to determine a first angle between the first and second jaw members.

20 Claims, 8 Drawing Sheets

Related U.S. Application Data (60) Provisional application No. 62/888,235, filed on Aug. 16, 2019.

(51) Int. Cl.
    *A61B 18/00*      (2006.01)
    *A61B 18/12*      (2006.01)
    *A61B 34/00*      (2016.01)

(52) U.S. Cl.
    CPC ............... *A61B 2018/0063* (2013.01); *A61B 2018/00875* (2013.01); *A61B 2018/1266* (2013.01); *A61B 2018/1455* (2013.01); *A61B 34/25* (2016.02)

(56) References Cited

U.S. PATENT DOCUMENTS

| | | |
|---|---|---|
| 8,591,506 B2 | 11/2013 | Wham et al. |
| 8,764,749 B2 | 7/2014 | McKenna et al. |
| 9,186,200 B2 | 11/2015 | Unger et al. |
| 9,474,570 B2 | 10/2016 | McKenna et al. |
| 10,245,104 B2 | 4/2019 | McKenna et al. |
| 11,931,097 B2 | 3/2024 | Fischvogt et al. |
| 2009/0261804 A1 | 10/2009 | McKenna et al. |
| 2014/0005640 A1 | 1/2014 | Shelton, IV et al. |
| 2014/0005662 A1* | 1/2014 | Shelton, IV ....... A61B 18/1445 606/41 |
| 2017/0086876 A1 | 3/2017 | Wiener et al. |
| 2017/0086910 A1 | 3/2017 | Wiener et al. |
| 2017/0105786 A1 | 4/2017 | Scheib et al. |
| 2017/0189101 A1 | 7/2017 | Yates et al. |
| 2017/0215944 A1 | 8/2017 | Keffeler |
| 2019/0008543 A1 | 1/2019 | Scoggins et al. |
| 2019/0201029 A1 | 7/2019 | Shelton, IV et al. |

FOREIGN PATENT DOCUMENTS

| | | |
|---|---|---|
| WO | 2016196196 A1 | 12/2016 |
| WO | 2018039181 A1 | 3/2018 |

OTHER PUBLICATIONS

Extended European Search Report issued in corresponding application EP 23219801.0 dated Apr. 22, 2024 (12 pages).

* cited by examiner

ELECTROSURGICAL INSTRUMENTS INCLUDING A JAW ANGLE DETECTION SYSTEM

CROSS-REFERENCE TO RELATED APPLICATIONS

This application is a divisional of U.S. patent application Ser. No. 16/944,367, filed on Jul. 31, 2020, now U.S. Pat. No. 11,931,097, which claims the benefit of the filing date of provisional U.S. Patent Application No. 62/888,235, filed on Aug. 16, 2019, the entire contents of each of which being incorporated herein by reference.

FIELD

The present technology is generally related to a surgical instrument, and more particularly to a surgical instrument with a jaw angle detection system.

BACKGROUND

End effectors utilize mechanical action to constrict, grasp, dissect, and/or clamp tissue. Electrosurgical end effectors utilize both mechanical clamping action and electrical energy to effect hemostasis by heating the tissue and blood vessels. By controlling the intensity, frequency, and duration of the electrosurgical energy applied through the jaw members to the tissue, the surgeon can coagulate, cauterize, and/or seal tissue.

In order to effect a proper seal with larger vessels or thick tissue, two predominant mechanical parameters should be accurately controlled: the pressure applied to the tissue; and the gap distance between the electrodes. Both of these parameters may be affected by the thickness of vessels or tissue. More particularly, accurate application of pressure is important for several reasons: to reduce the tissue impedance to a low enough value that allows enough electrosurgical energy through the tissue; to overcome the forces of expansion during tissue heating; and to contribute to the end tissue thickness, which is an indication of an effective seal.

SUMMARY

In one aspect, the present disclosure provides an electrosurgical instrument including an elongated shaft, an end effector, a drive shaft, and a switch assembly. The end effector is coupled to a distal end portion of the elongated shaft and includes opposing first and second jaw members. The end effector is configured to move between an open configuration, in which the first and second jaw members define a first gap therebetween. The end effector is configured to move between a closed configuration, in which the first and second jaw members define a second gap therebetween, smaller than the first gap. The drive shaft is operably coupled to the end effector to move the end effector between the open and closed configurations. Switch assembly includes a first electrical contact and a second electrical contact. The first electrical contact is coupled to the drive shaft and configured to move with the drive shaft. The second electrical contact is configured to be engaged by the first electrical contact in response to a movement of the drive shaft to determine a first angle between the first and second jaw members.

In aspects, the first electrical contact may be a coil spring.

In aspects, the coil spring may extend proximally from the drive shaft.

In aspects, the coil spring may have a distal end portion coupled to the drive shaft, and a proximal end portion configured to engage the first electrical contact upon the end effector moving to a position between the open and closed configurations.

In aspects, the switch assembly may further include a third electrical contact coupled to the drive shaft. The third electrical contact may be configured to move with the drive shaft to engage the second electrical contact in response to movement of the drive shaft to determine a second angle between the first and second jaw members.

In aspects, the first and third electrical contacts may be coil springs and the third electrical contact may have a reduced length compared to the first electrical contact.

In aspects, the third electrical contact may be disposed within the first electrical contact.

In aspects, the first and third electrical contacts may extend proximally from the drive shaft.

In aspects, each of the first and third electrical contacts may have a distal end portion coupled to the drive shaft, and a proximal end portion. The proximal end portion of the first electrical contact may be configured to engage the second electrical contact upon the end effector moving to a first position between the open and closed configurations. The proximal end portion of the third electrical contact may be configured to engage the second electrical contact upon the end effector moving to a second position between the open and closed configurations.

In aspects, the electrosurgical instrument may further include a handle housing having the elongated shaft extending distally therefrom. The first electrical contact may be fixed within the handle housing.

In aspects, the second electrical contact may be disposed in the handle housing at a location distally of the first electrical contact.

In another aspect, the disclosure provides an electrosurgical instrument including an elongated shaft, an end effector, a drive shaft, a detecting circuit, and an electrical contact. The end effector is coupled to a distal end portion of the elongated shaft. The end effector includes opposing first and second jaw members configured to move between an open configuration, in which the first and second jaw members define a first gap therebetween. The end effector is configured to move between a closed configuration, in which the first and second jaw members define a second gap therebetween, smaller than the first gap. The drive shaft is operably coupled to the end effector to move the end effector between the open and closed configurations. The detecting circuit having a plurality of contacts. The electrical contact is coupled to the drive shaft and configured to move with the drive shaft, such that the electrical contact moves relative to the detecting circuit. Each discrete position of the electrical contact relative to a respective contact of the plurality of contacts of the detecting circuit corresponds to a discrete angle between the first and second jaw members.

In aspects, the plurality of contacts of the detecting circuit may be co-linear along an axis.

In aspects, the axis may be parallel with an axis defined by the drive shaft.

In aspects, the plurality of contacts of the detecting circuit may be disposed in a linear array.

In aspects, the plurality of contacts of the detecting circuit may be nested with one another.

In aspects, a first contact of the plurality of contacts of the detecting circuit may be generally L-shaped and a second contact of the plurality of contacts of the detecting circuit may be generally Z-shaped.

In aspects, the plurality of contacts of the detecting circuit may include an L-shaped first contact, a linear-shaped second contact, and a third contact. The L-shaped first contact may have a long leg and a short leg extending transversely from the long leg. The linear-shaped second contact may be nested with the first contact. The third contact may be aligned with and disposed distally of the long leg of the first contact.

In aspects, the plurality of contacts of the detecting circuit may include a first contact and a second contact axially spaced from the first contact.

In aspects, the first contact may be configured to send a first signal to the generator in response to the electrical contact moving to a position in overlapping alignment with the first contact, and the second contact may be configured to send a second signal to a generator in response to the electrical contact moving to a position in overlapping alignment with the second contact. The first and second signals correspond to a discrete angle between the first and second jaw members.

In aspects, the electrical contact may be a variable resistor.

In another aspect, the disclosure provides a method of controlling operation of an electrosurgical instrument. Method includes grasping tissue between the first and second jaw members; determining an impedance of the tissue grasped between the first and second jaw members; determining an angle between the first and second jaw members; and delivering electrosurgical energy to the tissue grasped between the first and second jaw member based on the determined impedance and the determined angle.

In aspects, the method may further include determining a location of the grasped tissue along a length of the first and second jaw members based on the determined impedance and the determined angle.

In aspects, determining the angle may include receiving a signal at a first electrical contact from a second electrical contact. Second electrical contact may move relative to the first electrical contact a distance proportionate to a change in angle between the first and second jaw members as the first and second jaw members are clamped about the portion of the tissue.

The details of one or more aspects of the disclosure are set forth in the accompanying drawings and the description below. Other features, objects, and advantages of the techniques described in this disclosure will be apparent from the description and drawings, and from the claims.

As used herein, the terms parallel and perpendicular are understood to include relative configurations that are substantially parallel and substantially perpendicular up to about + or −10 degrees from true parallel and true perpendicular.

As used herein, the term "about" means that the numerical value is approximate and small variations would not significantly affect the practice of the disclosed embodiments. Where a numerical limitation is used, unless indicated otherwise by the context, "about" means the numerical value can vary by +10% and remain within the scope of the disclosed embodiments.

For the purposes herein, the term "voltage divider network" relates to any suitable form of resistive, capacitive, or inductive switch closure (or the like) that determines the output voltage across a voltage source (e.g., one of two impedances) connected in series. A "voltage divider" as used herein relates to a number of resistors connected in series that are provided with taps at certain points to make available a fixed or variable fraction of the applied voltage.

DETAILED DESCRIPTION

Embodiments of the presently disclosed electrosurgical instrument are described in detail with reference to the drawings, in which like reference numerals designate identical or corresponding elements in each of the several views. As used herein, the term "distal" refers to that portion of the surgical instrument or component thereof, farther from the user, while the term "proximal" refers to that portion of the surgical instrument, or component thereof, closer to the user.

Figure 1:
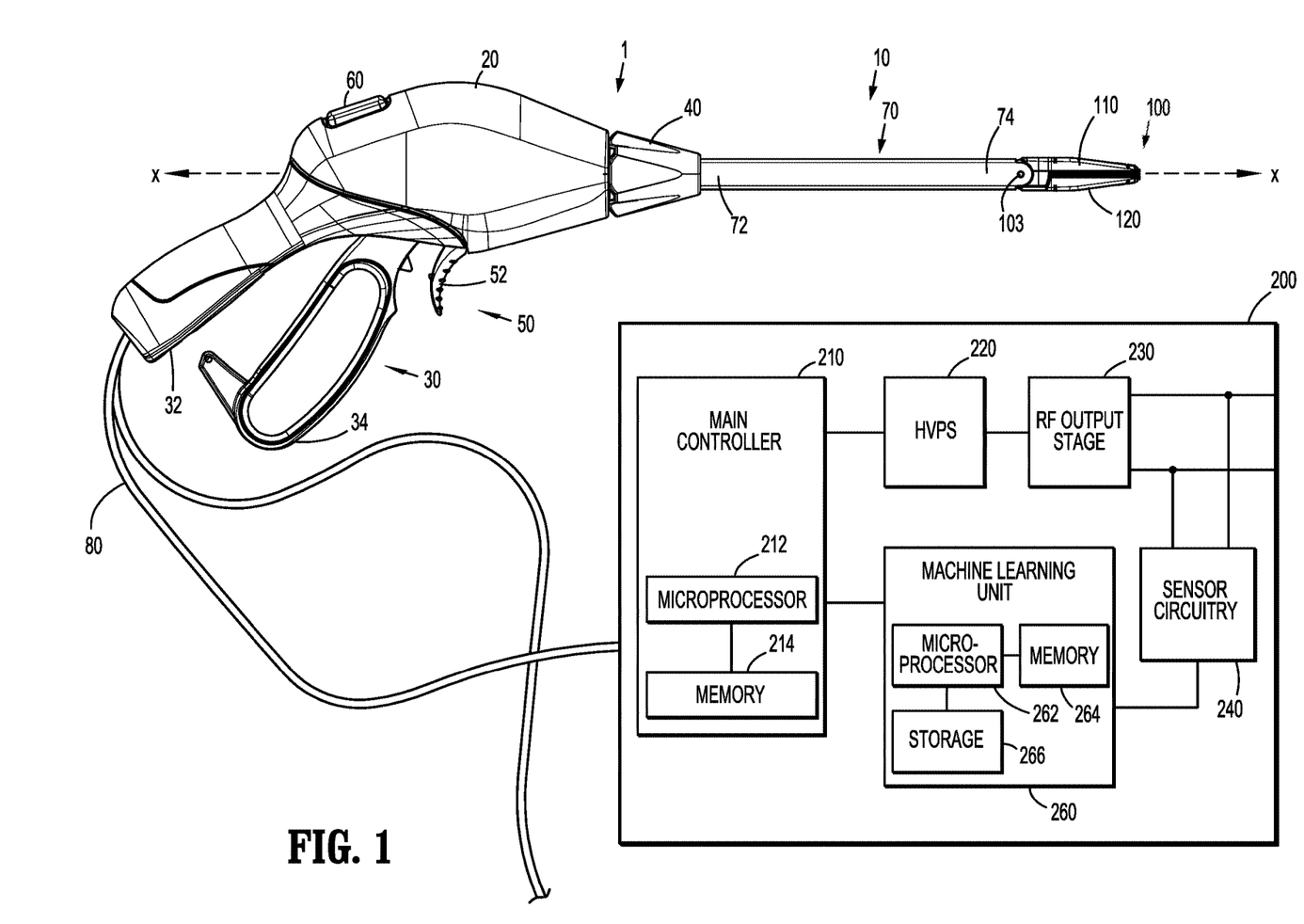
FIG. 1 is a side view illustrating a surgical system including a generator and an electrosurgical forceps according to an embodiment of the disclosure including a housing, a shaft assembly, and an end effector having a pair of jaw members in an approximated configuration.
Figure 2:
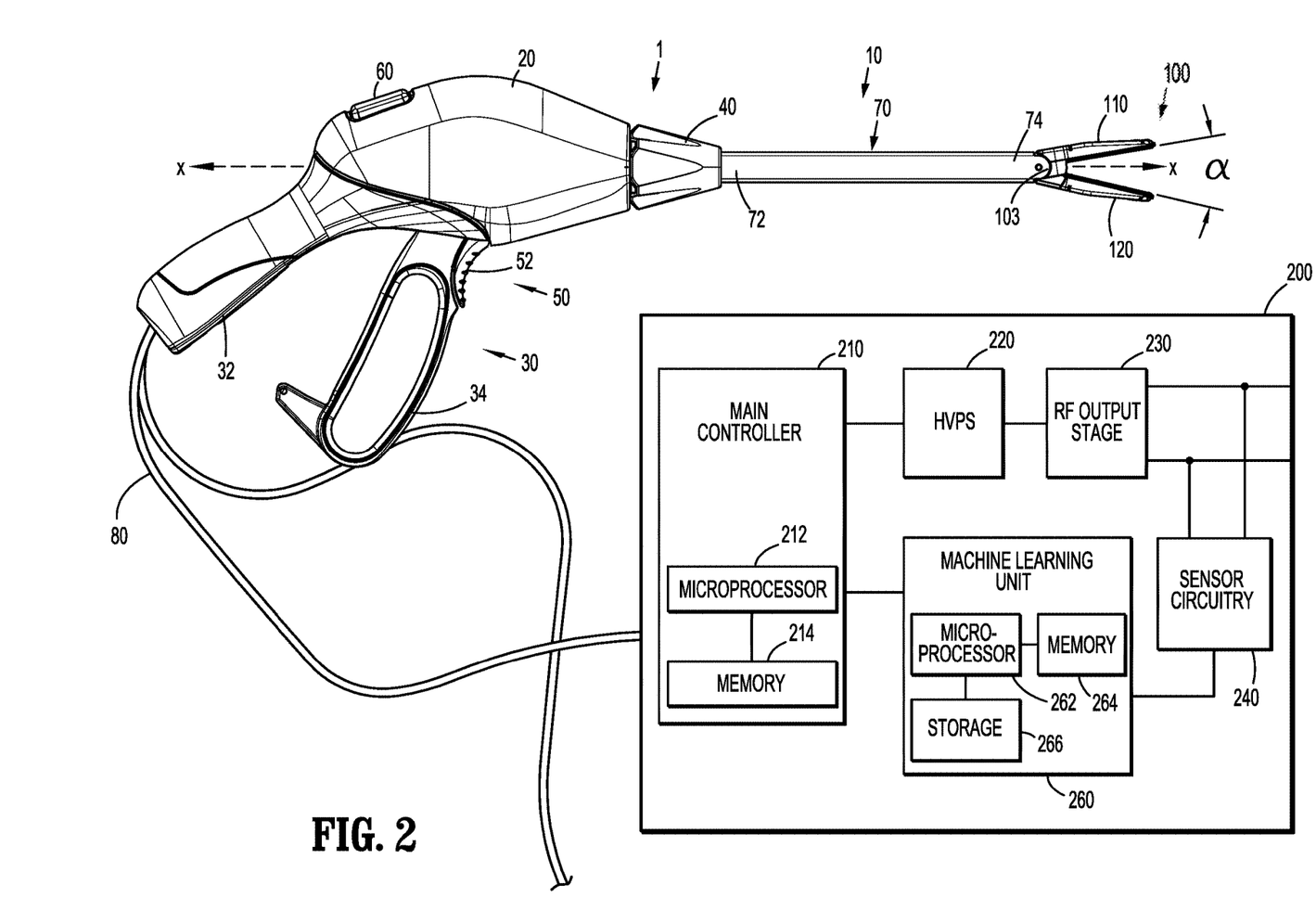
FIG. 2 is a side view of the surgical system of FIG. 1 depicted with the pair of jaw members of the electrosurgical forceps in an expanded configuration.

With reference to FIGS. 1 and 2, a surgical system 1 is provided in accordance with the present disclosure. Surgical system 1 includes an energy-based surgical instrument, such as, for example, an endoscopic forceps 10, coupled to a generator 200. Either a laparoscopic, an endoscopic, or an open instrument (not explicitly shown) may be utilized in accordance with the present disclosure, however, different electrical and mechanical connections and considerations apply to each particular type of instrument. As detailed below, surgical system 1 is configured to incorporate machine learning to facilitate the treatment of tissue, based on sensed data, thus providing more unique methods of treating tissue.

Forceps 10 defines a longitudinal axis "X" and includes a housing 20, a handle assembly 30, a rotating assembly 40, a trigger assembly 50, a switch 60, a shaft 70 extending distally from housing 20, and an end effector assembly 100. Shaft 70 has a proximal end portion 72 that mechanically engages housing 20 and a distal end portion 74 configured to mechanically engage end effector assembly 100. Housing 20 contains the internal working components of forceps 10. Reference may be made to commonly-owned U.S. Pat. No. 7,156,846, the entire contents of which are incorporated herein by reference, for a detailed description of the internal working components of housing 20.

End effector assembly 100 includes a pair of opposing jaw members 110 and 120 coupled to distal end portion 74 of shaft 70. Jaw members 110, 120 are moveable between a closed configuration (FIG. 1) wherein jaw members 110, 120 are approximated for grasping tissue therebetween and an open configuration (FIG. 2) wherein jaw members 110, 120 are spaced farther apart from one another. End effector assembly 100 is designed as a unilateral assembly, e.g., jaw member 120 is fixed relative to shaft 70, and jaw member 110 is moveable about a pivot 103 relative to shaft 70 and fixed jaw member 120. In some embodiments, end effector assembly 100 may be configured as a bilateral assembly, e.g., where both jaw member 110 and jaw member 120 are moveable about pivot 103 relative to one another and to shaft 70.

Forceps 10 also includes an electrosurgical cable 80 that connects forceps 10 to generator 200 or other suitable power source. In some embodiments, forceps 10 may be configured as a battery-powered instrument. Cable 80 includes a wire or wires (not explicitly shown) extending therethrough that has sufficient length to extend through shaft 70 in order to provide electrical energy to at least one of jaw members 110 and 120 of end effector assembly 100. Trigger 52 of trigger assembly 50 may be selectively depressed to advance a knife (not explicitly shown) between jaw members 110, 120 to cut tissue grasped therebetween. Switch 60 is selectively activated to supply electrosurgical energy to jaw members 110, 120.

Handle assembly 30 includes a fixed handle 32 and a moveable handle 34. Fixed handle 32 is integrally associated with housing 20 and moveable handle 34 is moveable relative to fixed handle 32. Rotating assembly 40 is rotatable in either direction about longitudinal axis "X" to rotate end effector 100 about longitudinal axis "X." Moveable handle 34 of handle assembly 30 is coupled to a drive shaft 76 (FIG. 3) that, together, mechanically cooperate to cause movement of one or both of jaw members 110 and 120 between the open configuration and the closed configuration to grasp tissue disposed between jaw members 110, 120. Moveable handle 34 is biased from fixed handle 32 and correspondingly biases jaw members 110, 120 toward the open configuration. Moveable handle 34 is movable from an unactuated position (e.g., spaced from fixed handle 32) to an actuated position (e.g., approximating fixed handle 32) to move jaw members 110, 120 from the open configuration to the closed configuration.

Figure 3:
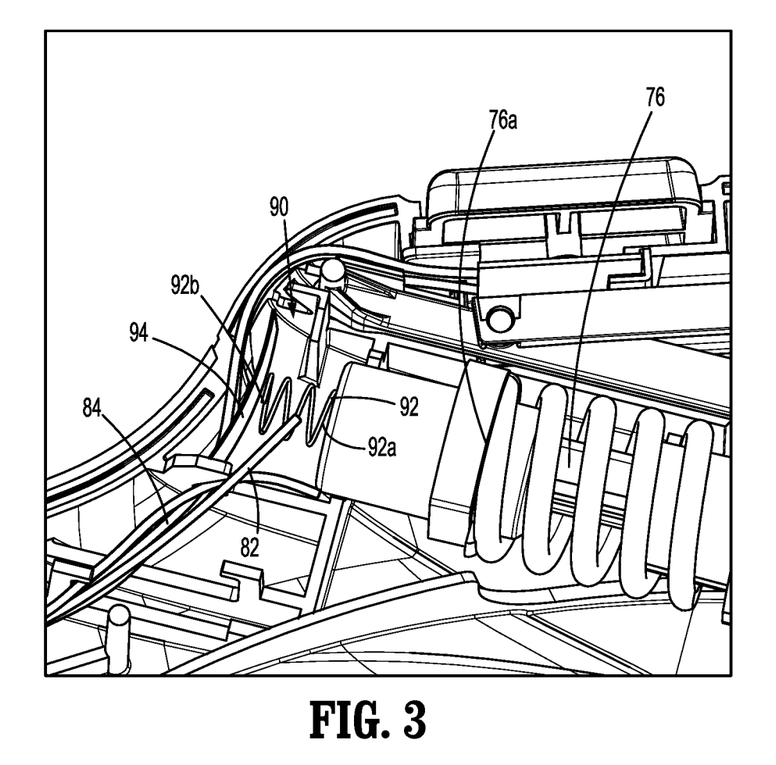
FIG. 3 is an enlarged, perspective view of the proximal portion of the forceps of FIG. 1 with a portion of the housing removed revealing internal components including a switch assembly having a spring coil and an electrical contact.
Figure 4:
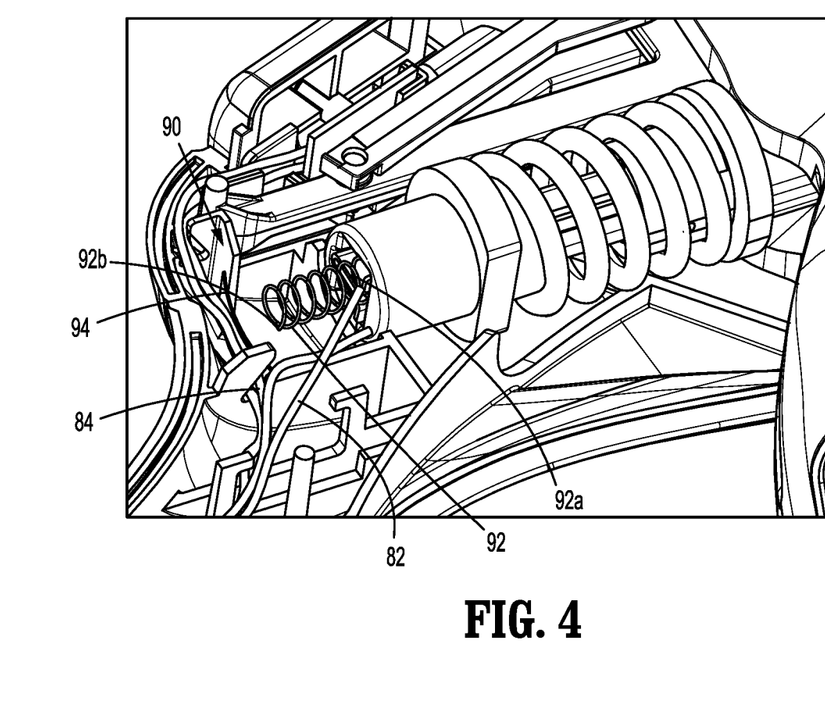
FIG. 4 is a perspective view of the proximal portion of the forceps of FIG. 1, with a portion of the housing removed, illustrating the spring coil and the electrical contact of the switch assembly in close proximity to one another.

With reference to FIGS. 3 and 4, in order to sense an angle between jaw members 110, 120, forceps 10 includes a switch assembly 90 having a first electrical contact 92 (e.g., a coil spring) and a second electrical contact 94 (e.g., a metal plate), each electrically coupled to generator 200. In some embodiments, first and second electrical contacts 92, 94 may communicate with generator 200 wirelessly.

Coil spring 92 of switch assembly 90 may be electrically coupled to generator 200 via a coil spring cable 82 which delivers a voltage source to coil spring 92. Coil spring 92 has a distal end portion 92a and a proximal end portion 92b. Distal end portion 92a of coil spring 92 is coupled to proximal end portion 76a of drive shaft 76 and extends proximally from drive shaft 76. Proximal end portion 92b of coil spring 92 is disposed in spaced relation from electrical contact 94 and is configured to engage electrical contact 94 in response to proximal movement of drive shaft 76. Electrical contact 94 of switch assembly 90 may be disposed within proximal portion of housing 20 and electrically coupled to generator 200 via an electrical contact cable 84.

Figures 5A, 5B, 5C:
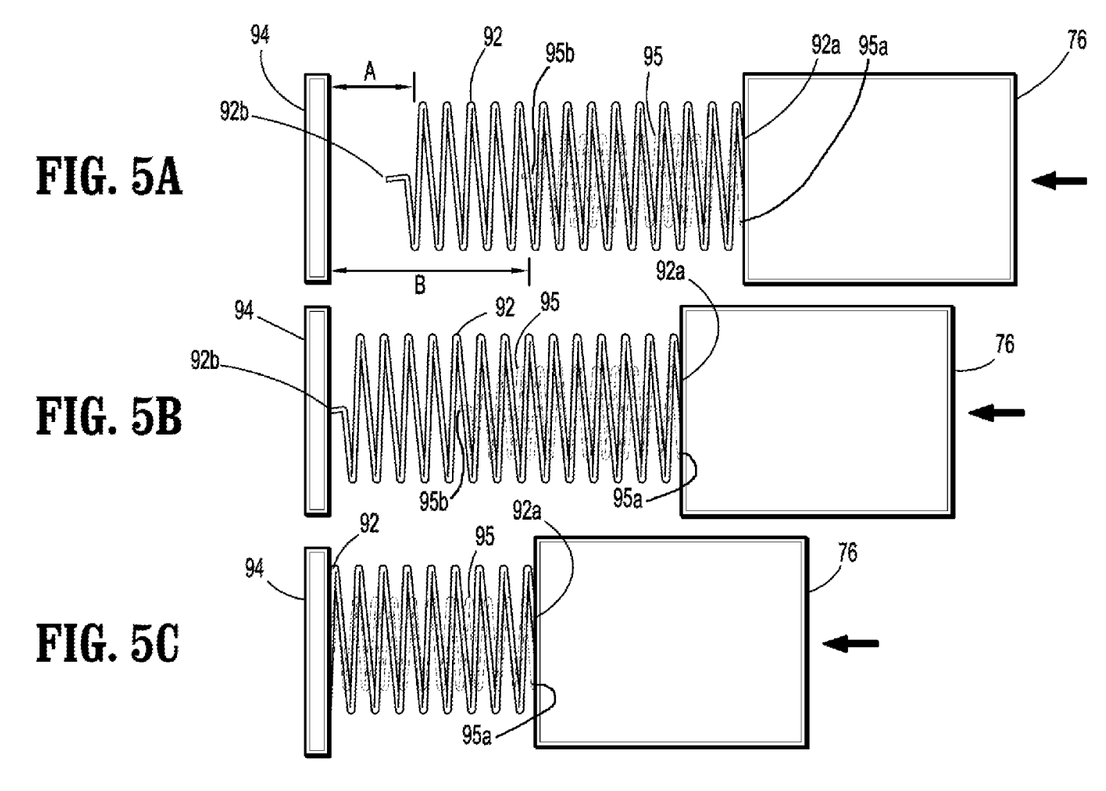
FIGS. 5A-5C are schematic illustrations of the switch assembly of FIG. 3, including an additional spring coil, depicted in different states.

With reference to FIGS. 5A-5C, switch assembly 90 may further include a second electrical contact, such as, for example, an additional coil spring 95 disposed within first coil spring 92. Coil spring 95 is electrically coupled to generator 200 via a cable (not shown) which delivers a voltage to coil spring 95. Coil spring 95 has a distal end portion 95a and a proximal end portion 95b. Distal end portion 95a of coil spring 95 is coupled to proximal end portion 76a of drive shaft 76. Coil spring 95 is nested within coil spring 92 and configured for independent contact with electrical contact 94. Coil spring 95 extends proximally from drive shaft 76 and is spaced further from electrical plate 94 than is coil spring 92. In aspects, switch assembly 90 may include any suitable number of coil springs, such as, for example, three or more. In other aspects, one or both of electrical contacts 92, 95 may be any suitable biasing member, such as, for example, an accordion spring, a wave spring, etc.

With reference to FIGS. 1 and 2, generator 200 generally includes a main controller 210, a high voltage DC power supply (HVPS) 220 (or other suitable power supply), an RF output stage 230 (or other suitable output depending on the energy delivered to end effector assembly 100), sensory circuitry 240, and a user interface (not shown), e.g., a graphical user interface to enable the input and display of information such as settings, warnings, treatment complete indicators, etc.

Main controller 210 includes a microprocessor 212 connected to a computer-readable storage medium or memory 214, which may be a volatile type memory, e.g., RAM, or a non-volatile type memory, e.g., flash media, disk media, etc. Main controller 210 is coupled to power supply 220 and/or RF output stage 230, thus allowing microprocessor 212 to control the output of energy from generator 200 to end effector assembly 100. Microprocessor 212 is further coupled to sensory circuitry 240 for receiving feedback signals from end effector assembly 100 to perform feedback-based control of the delivery of energy to forceps 10, as detailed below. Memory 214 may store suitable instructions, to be executed by microprocessor 212, for indicating the sequence, duration, and/or parameters associated with the energy delivery from generator 200 to end effector assembly 100 to treat tissue. In some embodiments, generator 200 is configured to supply energy to end effector assembly 100 according to a tissue sealing algorithm such that the supply of energy, together with the mechanical parameters of end effector assembly 100, e.g., impedance of the tissue and jaw gap, enable the scaling of tissue grasped between jaw members 110, 120. However, other suitable tissue treatment effects are also contemplated.

Sensory circuitry 240 is coupled to suitable sensor components for measuring and providing feedback with respect to a variety of tissue and/or energy parameters, for example, switch assembly 90. In addition to being coupled to switch assembly 90, sensory circuitry 240 is coupled to electrical leads (not shown) for sensing additional properties of the tissue grasped between jaw members 110, 120 or the energy conducted therethrough prior to or during tissue treatment. Sensory circuitry 240, for example, may further be configured to sense the impedance of tissue grasped between jaw members 110, 120 during the conduction of energy between tissue-contacting plates (not shown) and/or to sense power during the conduction of energy between tissue-contacting plates. For a detailed description of utilizing impedance-sensing during tissue treatment, reference may be made to commonly-owned U.S. Pat. Nos. 8,034,049, 9,186,200, and 8,591,506, the entire contents of each of which are incorporated herein by reference.

Machine learning unit 260 includes a microprocessor 262 connected to a computer-readable storage medium or memory 264, which may be a volatile type memory, e.g., RAM, or a non-volatile type memory, e.g., flash media, disk media, etc. Memory 264 stores suitable instructions, to be executed by microprocessor 262, for receiving the sensed data from sensory circuitry 240, accessing storage device 266 of machine learning unit 260, determining tissue information based upon the sensed data and information stored in storage device 266, and providing feedback to main controller 210 based upon the determined tissue information. Although illustrated as part of generator 200, it is also contemplated that machine learning unit 260 may be remote from generator 200, e.g., on a remote server, and accessible by generator 200 via a wired or wireless connection. In embodiments where machine learning unit 260 is remote, it is contemplated that machine learning unit 260 may be accessible by and connected to multiple generators.

Storage device 266 of machine learning unit 260 stores one or more machine learning applications, e.g., algorithms and/or models, configured to determine tissue information based upon the sensed data received from sensory circuitry 240. Machine learning application(s) are trained on and learn from experimental data and/or data from previous procedures initially input into the one or more machine learning applications in order to enable the machine learning application(s) to identify tissue information based upon such sensed data. Such sensed data may include tissue impedance data, power data, and/or any other suitable data. Suitable machine learning applications include, for example, Support Vector Machines (SVMs), applications employing Principle Component Analysis, Hidden Markov Models (HMMs), applications employing the Monte Carlo Method, etc.

In operation, referring to FIGS. 5A-5C, prior to treatment of the tissue, moveable handle 34 (FIG. 1) is biased from fixed handle 32 to bias jaw members 110, 120 towards the open configuration such that tissue may be disposed between jaw members 110, 120. Moveable handle 34 is moved from the unactuated position towards the actuated position to pivot jaw members 110, 120 from the open configuration to the closed configuration for grasping tissue therebetween.

Since moveable handle 34 of handle assembly 30 is coupled to drive shaft 76 (FIG. 3), and coil springs 92, 95 are coupled to drive shaft 76, coil springs 92, 95 move in response to movement of drive shaft 76. In particular, as drive shaft 76 moves proximally towards electrical contact 94, a distance indicated by "A" in FIG. 5A, coil spring 92 first engages electrical contact 94. Voltage delivered from generator 200 through coil spring 92 is received by electrical contact 94 to provide a feedback signal to sensory circuitry 240 (FIGS. 1 and 2) of generator 200. Using an algorithm stored in, for example, memory 214, the jaw angle α between jaw members 110, 120 is determined using the feedback signal. In some embodiments, sensory circuitry 240 delivers the feedback signal to machine learning unit 260, which determines the jaw angle α between jaw members 110, 120 based on the feedback signal received by sensory circuitry 240.

To change the jaw angle α from a first jaw angle to a second jaw angle, a further actuation of moveable handle 34 further retracts drive shaft 76, thereby compressing coil spring 92 against electrical contact 94 and approximating proximal end of coil spring 95 closer to electrical contact 94. Upon moving coil spring 95 a distance indicate by "B" in FIG. 5A, coil spring 95 contacts electrical contact 94. Voltage source delivered from generator 200 through coil spring 95 is received by electrical contact 94 to provide a feedback signal to sensory circuitry 240 (FIGS. 1 and 2) of generator 200. Sensory circuitry 240 delivers the feedback signal to machine learning unit 260 which determines the second jaw angle between jaw members 110, 120 based on the feedback signal received by sensory circuitry 240.

Prior to tissue treatment, and with the tissue grasped between jaw members 110, 120, an impedance sensor in jaw members 110, 120 may sense impedance of the tissue and send the detected impedance to sensory circuitry 240. The jaw angle α and the impedance signals which are received by sensory circuitry 240 are relayed to machine learning unit 260. Machine learning unit 260, based upon the jaw angle α, the impedance, and any other sensed data received from sensory circuitry 240, determines tissue information using the machine learning application(s) stored in storage device 266 of machine learning unit 260. Tissue information may include, for example, where the tissue is placed within jaw members 110, 120 (e.g., grasped at the tip or heel of the jaw members 110, 120), tissue density, tissue thickness (based on relative resistance to jaw closure), speed of jaw closure, jaw members 110, 120 being in the appropriate configuration, a "re-grasp" condition, and/or overall adequacy of the tissue seal either prior to, during, or after activation.

Tissue information is relayed to main controller 210, and main controller 210 may output an alert and/or warning regarding the jaw angle α, or implement a feedback-based control of the delivery of electrosurgical energy to end effector assembly 100. In particular, power supply 220 and RF output stage 230, based on control signals received from microprocessor 212 of main controller 210, cooperate to deliver a selected amount of electrosurgical energy to tissue-contacting plates of jaw members 110, 120 via electrical leads to treat tissue grasped between jaw members 110, 120. The amount of electrosurgical energy delivered is selected based on the tissue information determined by machine learning unit 260.

Feedback-based control of the delivery of energy to forceps 10 may be implemented according to the parameter-based tissue grouping, e.g., tissue associated with a particular sensed parameter and/or similarity-based tissue grouping, e.g., separating tissue into groups based upon similarities and differences. For example, the feedback-based control may group together tissues with the same impedance, the same jaw angle α, the same impedance and jaw angle α, the same impedance and different jaw angle α, a different impedance and same jaw angle α, or any combination thereof, to deliver energy to forceps 10 according to each grouping. Other forms of feedback-based controls are contemplated, such as, for example treating tissue grasped at the tip differently than tissue grasped at the heel, treating tissue based on the determined state of diseased or challenged tissues without advanced sensors, adjusting energy delivery based on the monitored jaw angle α during tissue sealing accounting for changes in the jaw angle α, preventing delivery of energy based on potential errors during tissue sealing e.g., exceeding a jaw angle threshold.

Figure 6:
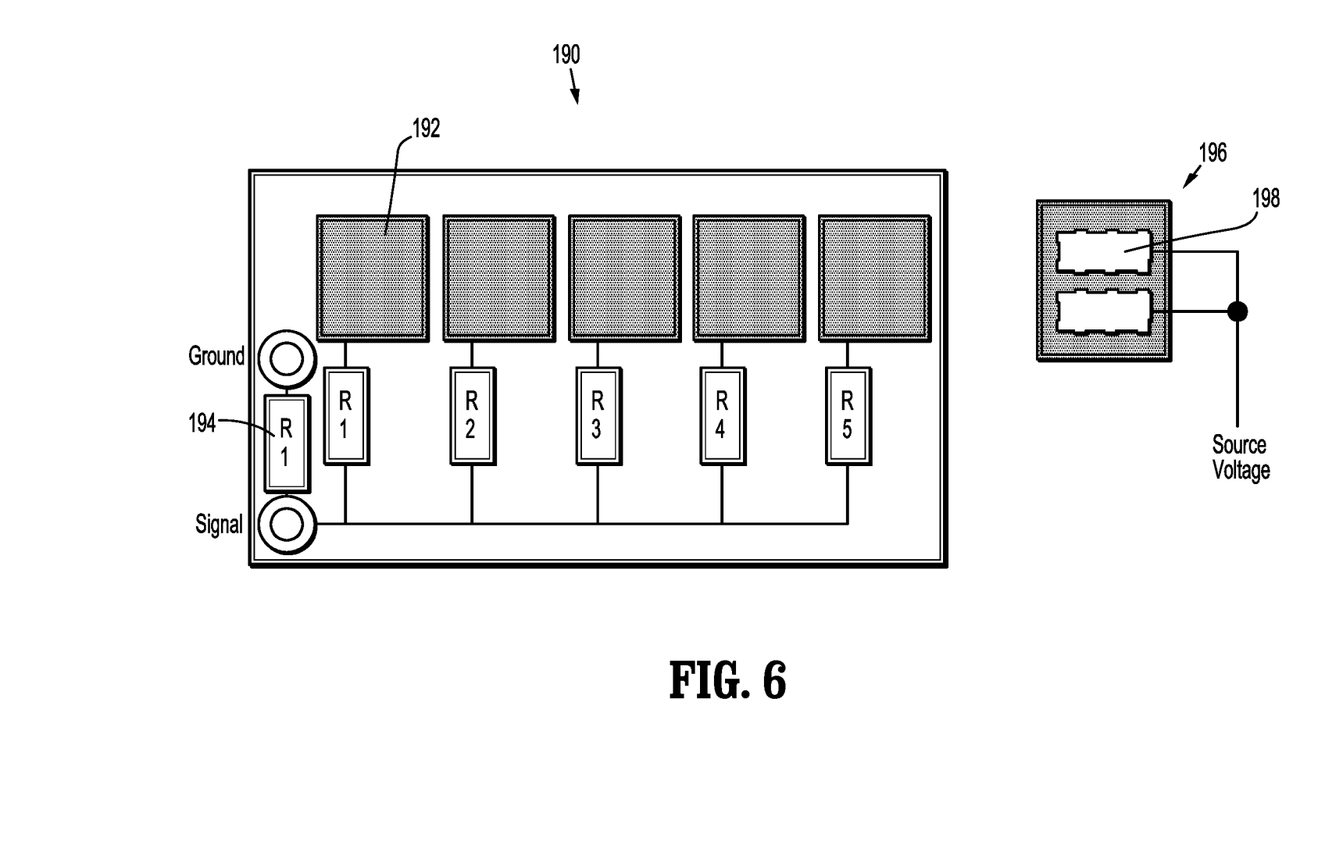
FIG. 6 is a schematic illustration of another embodiment of a switch assembly for use in the forceps of FIG. 1 including an electrical contact and a detecting circuit having contacts axially spaced from one another.
Figure 7:
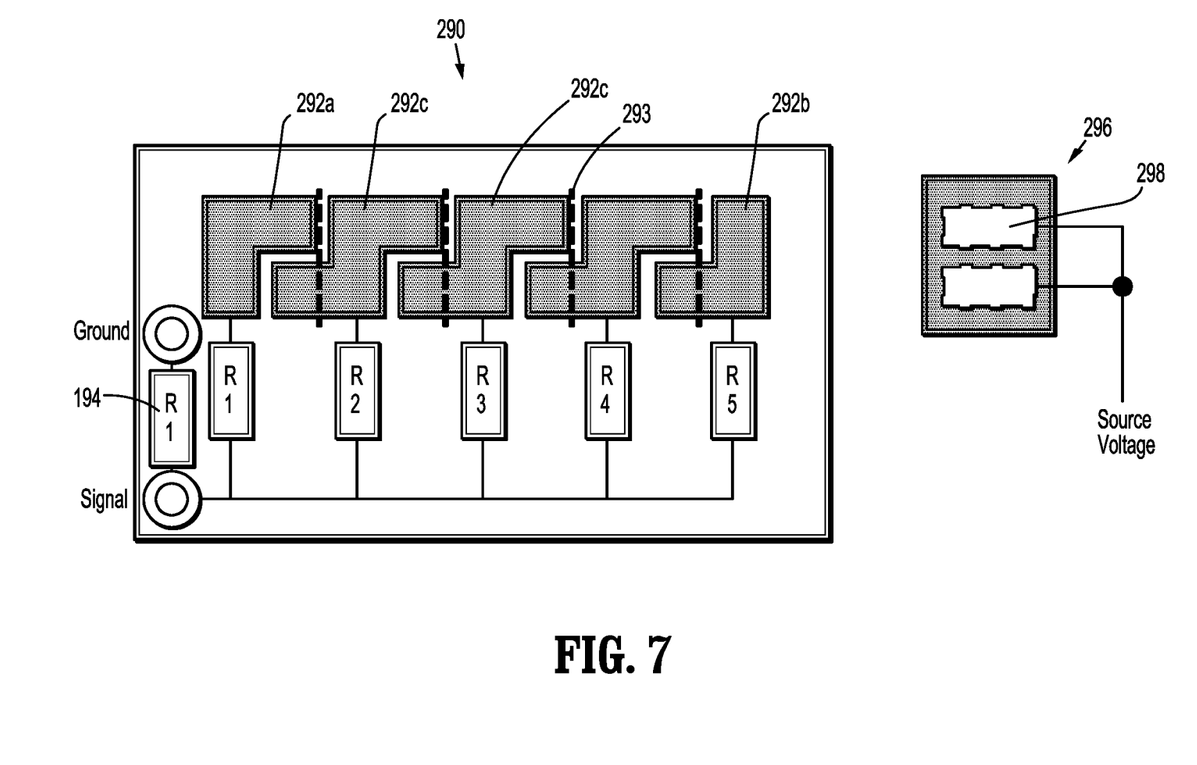
FIG. 7 is a schematic illustration of another embodiment of a switch assembly for use in the forceps of FIG. 1.
Figure 8:
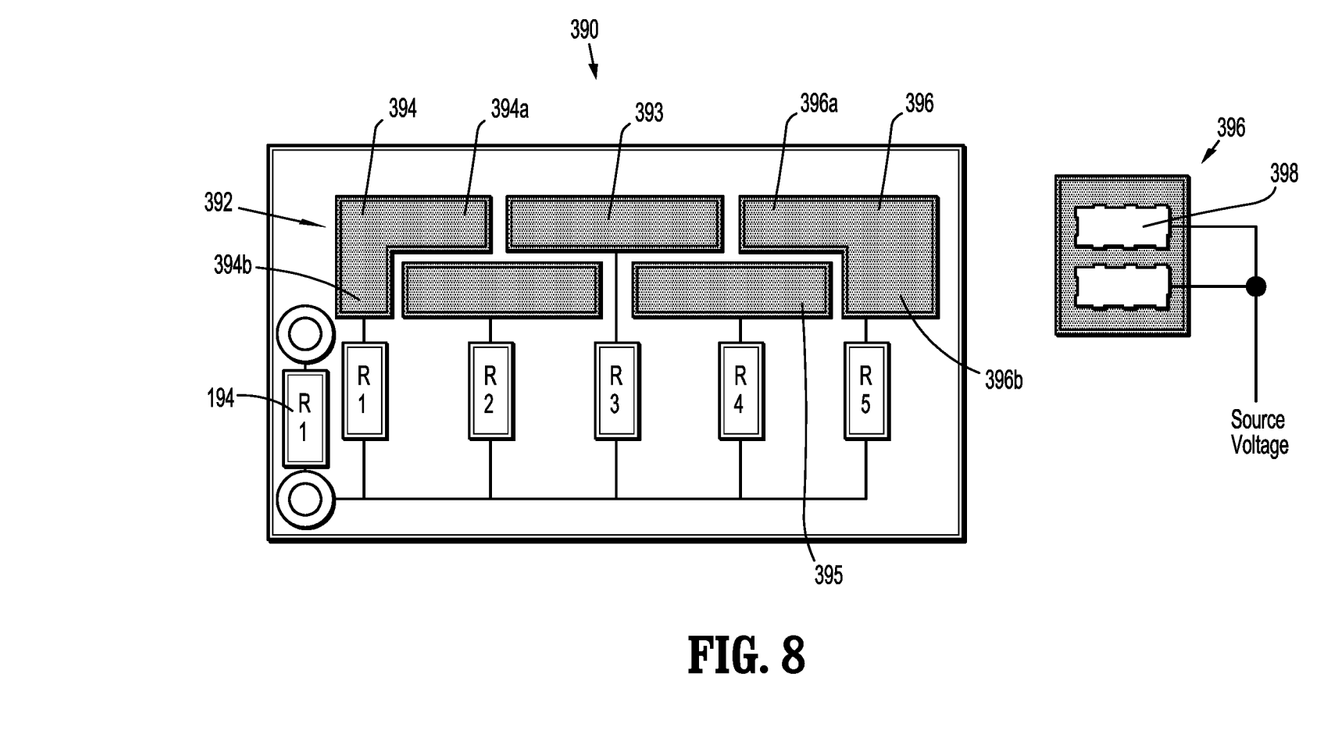
FIG. 8 is a schematic illustration of another embodiment of a switch assembly for use in the forceps of FIG. 1.

FIGS. 6-8 illustrate alternative embodiments of a switch assembly for detecting a jaw angle of forceps 10. With reference to FIG. 6, forceps 10 includes a detecting circuit 190 and an electrical contact 196. Detecting circuit 190 includes a plurality of contacts 192 disposed along an axis and in series, e.g., in a linear array. Each contact 192 is coupled to a variable resistor 194, each representing a discrete angle of jaw members 110, 120, e.g., a voltage divider network, corresponding to the jaw angle α. Each variable resistor 194 delivers, to generator 200, a feedback signal indicative of the discrete angle corresponding to the jaw angle α between jaw members 110, 120.

Electrical contact 196 has two conductive plates 198 in parallel and is disposed along drive shaft 76 (FIG. 4). For example, electrical contact 196 may be attached to drive shaft 76, such that movement of drive shaft 76 results in a corresponding movement of electrical contact 196. Electrical contact 196 receives the voltage delivered from generator 200 and the voltage is delivered via conductive plates 198 to detecting circuit 190.

In operation, drive shaft 76 is retracted proximally in response to movement of moveable handle 34 toward the actuated position, thereby moving jaw members 110, 120 from the open configuration to the closed configuration. Since electrical contact 196 is coupled to drive shaft 76, electrical contact 196 moves with drive shaft 76 from a starting position, corresponding to the open configuration of jaw members 110, 120, toward detecting circuit 190. Electrical contact 196 moves across plurality of contacts 192, whereby the intensity of the feedback is varied. A feedback signal corresponding to the jaw angle α is produced upon movement of electrical contact 196 into parallel with contacts 192. The feedback signal is then sent to sensory circuitry 240 for determination of the jaw angle α.

FIG. 7 illustrates another embodiment of a detecting circuit 290, similar to detecting circuit 190 of FIG. 6. Detecting circuit 290 includes a plurality of contacts 292 nested within one another to account for potential "dead spots." "Dead spots" is the spacing between the plurality of contacts, thus the location between the spacing of the plurality of contacts would not be detectable due to the lack of contacts present. In particular, the plurality of contacts 292 includes generally "L-shaped" outer contacts 292a, 292b and complementary generally "Z-shaped" contacts 292c nested in series with "L-shaped" contacts 292a, 292b. As electrical contact 296 moves across detecting circuit 290, the plurality of contacts 292 detect switch over points 293. Due to the shapes of the plurality of contacts, the "dead spots" are replaced with portions of the plurality of contacts thus the switch over points provide the ability to determine location between the plurality of contacts where "dead spots" would otherwise be located. Thus, the detection of switch over points 293 provides a more precise detection of the jaw angle α as jaw members 110, 120 move from the open configuration to the closed configuration, and vice versa.

FIG. 8 illustrates yet another embodiment of a detecting circuit 390, similar to detecting circuit 290 of FIG. 7. Detecting circuit 390 includes a plurality of contacts 392. The plurality of contacts 392 includes two generally "L-shaped" outer contacts 394, 396 each having a long leg 394a, 396a and a short leg 394b, 396b extending transversely from the long legs 394a, 396a, respectively. The plurality of contacts 392 also includes linear shaped contacts 392 that are cascaded and nested between outer contacts 394, 396. First linear contact 393 is disposed between long legs 394a, 396a of outer contacts 394, 396, and a pair of second linear contacts 395 is disposed between short legs 394b, 396b of outer contacts 394, 396.

Although the disclosure is directed towards sensing a jaw angle in conjunction with an electrosurgical instrument, the principles of the present disclosure may also be used in conjunction with any suitable type of instrument having jaws that open and close, such as ultrasonic instruments.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical instrument, comprising:
    an elongated shaft defining a longitudinal axis;
    a pair of jaw members disposed at a distal end of the elongated shaft;
    a drive shaft disposed within the elongated shaft and operably coupled to the pair of jaw members, wherein movement of the drive shaft along the longitudinal axis transitions the pair of jaw members between an open position and a closed position;
    a detecting circuit configured to detect an angle between the pair of jaw members, the detecting circuit including:
        a plurality of contacts disposed in a linear array along the longitudinal axis; and
        a plurality of resistors, each resistor of the plurality of resistors coupled to a respective contact of the plurality of contacts; and
    an electrical contact disposed on the drive shaft and including a pair of conductive plates configured to deliver a voltage to the detecting circuit, wherein the electrical contact is configured to move with the drive shaft along the longitudinal axis and relative to the detecting circuit such that an angle between the pair of jaw members is determined based on a position of the electrical contact along the longitudinal axis relative to the plurality of contacts of the detecting circuit.

2. The surgical instrument according to claim 1, wherein the plurality of contacts of the detecting circuit are axially spaced from each other along the longitudinal axis.

3. The surgical instrument according to claim 1, wherein the plurality of resistors is a plurality of variable resistors.

4. The surgical instrument according to claim 1, wherein the surgical instrument is an electrosurgical forceps configured to deliver electrosurgical energy to the tissue grasped between the pair of jaw members.

5. The surgical instrument according to claim 1, wherein the plurality of contacts includes at least one generally L-shaped contact and at least one generally Z-shaped contact nested in series with the at least one generally L-shaped contact.

6. The surgical instrument according to claim 5, wherein the at least one generally L-shaped contact includes a pair of generally L-shaped contacts disposed on respective ends of the linear array and the at least one generally Z-shaped contact is disposed between and in nested series with the pair of generally L-shaped contacts.

7. The surgical instrument according to claim 5, wherein a portion of the at least one generally L-shaped contact overlaps with at least a portion of the at least one generally Z-shaped contact along the longitudinal axis.

8. The surgical instrument according to claim 1, wherein the plurality of contacts includes at least one generally L-shaped contact and at least one linear-shaped contact nested in series with the at least one generally L-shaped contact.

9. The surgical instrument according to claim 8, wherein at least a portion of the at least one generally L-shaped contact overlaps with at least a portion of the at least one linear-shaped contact along the longitudinal axis.

10. The surgical instrument according to claim 8, wherein the at least one generally L-shaped contact includes a pair of generally L-shaped contacts disposed on respective ends of the linear array and the at least one linear-shaped contact is disposed between and in nested series with the pair of generally L-shaped contacts.

11. The surgical instrument according to claim 10, wherein each generally L-shaped contact of the pair of generally L-shaped contacts includes a long leg and a short leg extending transversely from the long leg.

12. The surgical instrument according to claim 11, wherein the at least one linear-shaped contact includes a first linear-shaped contact disposed between the long legs of the pair of generally L-shaped contacts and a second linear-shaped contact disposed between the short legs of the pair of generally L-shaped contacts.

13. A surgical instrument, comprising:
a pair of jaw members disposed at a distal end of an elongated shaft;
a drive shaft operably coupled to the pair of jaw members and defining a longitudinal axis, wherein movement of the drive shaft along the longitudinal axis transitions the pair of jaw members between an open position and a closed position;
a detecting circuit configured to detect an angle between the pair of jaw members, the detecting circuit including a plurality of contacts disposed in a linear array along the longitudinal axis; and
an electrical contact disposed on the drive shaft and including a pair of conductive plates configured to deliver a voltage to the detecting circuit, the electrical contact configured to move with the drive shaft along the longitudinal axis and relative to the detecting circuit such that an angle between the pair of jaw members is determined based on a position of the electrical contact along the longitudinal axis relative to the plurality of contacts of the detecting circuit.

14. The surgical instrument according to claim 13, wherein the detecting circuit includes a plurality of resistors, each resistor of the plurality of resistors coupled to a respective contact of the plurality of contacts.

15. The surgical instrument according to claim 13, wherein the surgical instrument is an electrosurgical forceps configured to deliver electrosurgical energy to the tissue grasped between the pair of jaw members.

16. The surgical instrument according to claim 13, wherein the plurality of contacts includes at least one generally L-shaped contact and at least one generally Z-shaped contact nested in series with the at least one generally L-shaped contact.

17. The surgical instrument according to claim 16, wherein the at least one generally L-shaped contact includes a pair of generally L-shaped contacts disposed on respective ends of the linear array and the at least one generally Z-shaped contact is disposed between and in nested series with the pair of generally L-shaped contacts.

18. The surgical instrument according to claim 13, wherein the plurality of contacts includes at least one generally L-shaped contact and at least one linear-shaped contact nested in series with the at least one generally L-shaped contact.

19. The surgical instrument according to claim 18, wherein the at least one generally L-shaped contact includes a pair of generally L-shaped contacts disposed on respective ends of the linear array and the at least one linear-shaped contact is disposed between and in nested series with the pair of generally L-shaped contacts.

20. A surgical instrument, comprising:
a pair of jaw members disposed at a distal end of an elongated shaft;
a drive shaft operably coupled to the pair of jaw members and defining a longitudinal axis, wherein movement of the drive shaft along the longitudinal axis transitions the pair of jaw members between an open position and a closed position;
a detecting circuit configured to detect an angle between the pair of jaw members, the detecting circuit including a plurality of contacts disposed in a linear array along the longitudinal axis; and
an electrical contact disposed on the drive shaft and configured to move with the drive shaft along the longitudinal axis and relative to the detecting circuit such that an angle between the pair of jaw members is determined based on a position of the electrical contact along the longitudinal axis relative to the plurality of contacts of the detecting circuit.

* * * * *